United States Patent [19]

Foell et al.

[11] 3,992,530

[45] Nov. 16, 1976

[54] [D-2-(1,4-CYCLOHEXADIENYL)GLY]⁶-DES-GLY¹⁰-LRH NONAPEPTIDE AMIDES

[75] Inventors: Theodore J. Foell, King of Prussia; Richard W. A. Rees, Bryn Mawr, both of Pa.

[73] Assignee: American Home Products Corporation, New York, N.Y.

[22] Filed: Dec. 8, 1975

[21] Appl. No.: 638,385

[52] U.S. Cl. .............................. 424/177; 260/78 A; 260/112.5 LH
[51] Int. Cl.² ................. C07C 103/52; A61K 37/00
[58] Field of Search ................. 260/78 A, 112.5 LH; 424/177

[56] References Cited
UNITED STATES PATENTS 3,901,872   8/1975   McKinley et al. .......... 260/112.5 LH

*Primary Examiner*—Lewis Gotts
*Assistant Examiner*—Reginald J. Suyat
*Attorney, Agent, or Firm*—Richard K. Jackson

[57] ABSTRACT

Compounds of the formula:

L-p-Glu-L-His-L-Trp-L-Ser-L-Tyr-D-2-(1,4-hexadienyl)Glyin which $R^4$ and $R^5$ are methyl or $R^4$ is hydrogen and $R^5$ is alkyl of 1 to 5 carbon atoms or phenethyl, or a non-toxic acid addition salt thereof, are claudogenic-interceptive agents useful in preventing or terminating pregnancy in mammals.

9 Claims, No Drawings

[D-2-(1,4-CYCLOHEXADIENYL)GLY]⁶-DES-GLY¹⁰-LRH NONAPEPTIDE AMIDES

DESCRIPTION OF THE INVENTION

In accordance with this invention there is provided a group of novel nonapeptides of the formula:

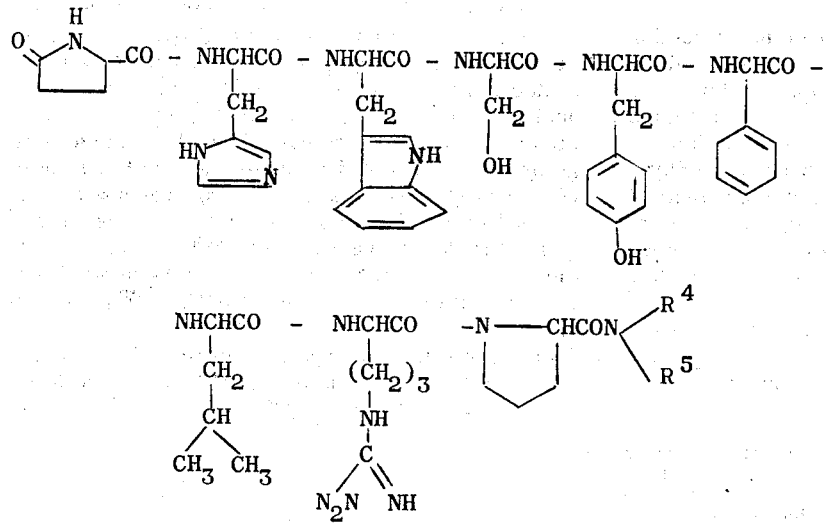

in which $R^4$ and $R^5$ are methyl or $R^4$ is hydrogen and $R^5$ is alkyl of 1 to 5 carbon atoms or phenethyl, or a non-toxic acid addition salt thereof. These compounds are anti-gravidity agents, the use thereof constituting an additional aspect of the invention, when administered to a female mammal after ovulation, in that they disrupt the normal physiological processes necessary for implantation and/or maintenance of the blastocyst.

The intermediates employed in the production of the anti-gravidity agents of this invention present an additional aspect of the invention. These intermediates are the fully protected polypeptide-resin and the fully protected polypeptide amides of the formula:

p-Glu-His(R)-Trp-Ser(R¹)-Tyr(R²)-D-2-(1,4-cyclohexadienyl)Gly -Leu-Arg(R³)-Pro-X in which X represents the OCH₂[polystyrene resin support] or $$-N\begin{matrix}R^4\\R^5\end{matrix}$$

where R-R⁵ are defined elsewhere in this disclosure.

The anti-gravidity agents of this invention, when administered to a female mammal, post-coitally pursuant to a daily regimen of at least about 600 micrograms per day per kilogram host body weight for a period in excess of three days, completely prevent pregnancy.

Although applicants do not wish to be bound by any specific theory of activity, they propose and believe, based upon studies conducted with a variety of animal models, that the nonapeptides of this invention exert a claudogenic/interceptive action via stimulation of the hypophysial-ovarian steriod axis.

In any event, regardless of the physiological pathway to the end result, the nonapeptides of this invention effectively prevent pregnancy in female mammals upon administration after coitus.

Hence the nonapeptides of this invention are useful as "morning-after" contraceptives to prevent or terminate pregnancy in the female mammal. Within this context, the nonapeptides may be used as anti-littering agents for control of rodent populations without use of rodenticides and their possible undesirable effect on other animals in the environment.

Pregnancy was avoided in the animal models by daily administration of the nonapeptide of this invention during the day 1 to 7 period after coitus as well as upon daily administration over the day 7 to day 12 period, post coitus. Thus both a claudogenic (pre-implantation) as well as an interceptive (post-implantation) type of interference with pregnancy was established.

The procedure followed in evaluating the anti-gravidity properties of the nonapeptides of this invention was as follows: Mature, female, Sprague-Dawley rats (350 ± 30 grams body weight) were caged with fertile male rats on the evening of proestrus. The presence of vaginal sperm the next morning was considered day 1 of pregnancy. The nonapeptide ethylamide, representative of the entire group of compounds of this invention, was administered subcutaneously in a corn oil vehicle on days 1–7, or 7–12 of pregnancy at a rate of 200 ug/rat/day. One-half the daily dose was administered at 9 A.M. and at 3 P.M. each day. The recipients of day 1–7 treatment were autopsied on day 14. The recipients of day 7–12 treatment were autopsied on day 18 of pregnancy. The effectiveness of the ethylamide and its effective dose was established by the absence of uterine implantation sites and fetuses. The presence of at least one normal fetus was considered to be the criterion of pregnancy. The claudogenic/interceptive activity of the nonapeptides of this invention was thereby established at a daily dose of about 600 micrograms per kilogram host body weight, the treatment being 100 per cent effective at a dose of 200 micrograms per rat per day in a six rat sample for each of the day 1–7 and day 7–12 periods.

For the purpose of defining the post coital stages of pregnancy in the rat as an experimental model, the following schedule is provided in definition of post-coital contraceptive activity which, for the purpose of this disclosure, is intended to embrace both pre-(claudogenic) and post-(interceptive) implantation contraceptive activity; day 1 - vaginal sperm; days 1–3 - ova transport in oviducts, fertilization; days 3–5 - blastocyst free in uterine lumen; days 5–7 - implantation into uterine wall; days > 7 – post implantation.

Based upon the findings of activity in the prevention of development of pregnancy in the rat model and the fact that present evidence indicates that the hormonal situation relating to the reproductive cycle up to and including ovulation, is basically the same in all female vertebrates, e.g. the human reproductive cycle is physiologically analogous with that of the rat, the activity of the nonapeptides of this invention effectively interferes with the development of the blastocyst pre- and post-implantation in the uterus in all mammals, including the human.

Thus, in accordance with the use aspect of this invention there is provided a method for preventing pregnancy in a mammal which comprises administering

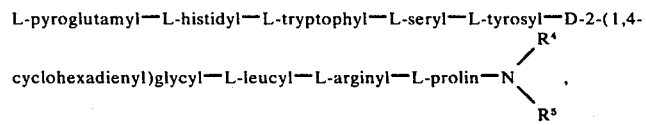

wherein $R^4$ and $R^5$ are defined supra, to said mammal, and post coitally, in a daily regimen containing at least about 600 micrograms per kilogram host body weight for a period sufficient to terminate said pregnancy. In operation, the anti-gravidity compound of this invention interferes with the mechanism of gestation, whether that interference is an early post-coital, pre-implantation contraceptive or as a post-implantation interceptive agent. Hence, the effective sequence of daily administration in the human is from day 1 of ovulation-fertilization to about day 6 to produce a claudogenic response, or from day 6 to about day 14 post ovulation - fertilization to effect an interceptive response in the gestational period. The human dose, based upon the posology of the experimental model, is approximately 28 milligrams per day for a fifty kilogram female.

The nonapeptides of this invention may be administered in any convenient form, orally or parenterally, with or without conventional pharmaceutical adjuvants well known to the art. In addition, conventional adducts of the nonapeptides may be employed to prolong its effectiveness, such as the protamine zinc or aluminum adducts which are prepared by conventional techniques.

The nonapeptides of this invention are prepared by solid phase methodology, following techniques generally known in the art for building an amino acid sequence from an initial resin supported amino acid. Merrifield, J.A.C.S. 85, 2149(1963) generally illustrates the technique involved.

The resin support employed may be any suitable resin conventionally employed in the art for the solid phase preparation of polypeptides, preferably polystyrene which has been cross-linked with from 0.5 to about 3-percent divinyl benzene, which has been chloromethylated to provide sites for ester formation with the initially introduced protected amino acid. The amino protected proline is coupled to the chloromethylated resin according to the procedure of Gisin, Helv. Chim. Acta., 56, 1476 (1973). Following the coupling of the amino protected proline to the resin support, the amino protecting group is removed by standard methods employing trifluoroacetic acid in methylene chloride, trifluoroacetic acid alone or HCl in dioxane. The deprotection is carried out at a temperature between about 0° C. and room temperature. After removal of the amino protecting group the remaining α-amino protected and, if necessary, side chain protected amino acids are coupled, seriatim, in the desired order to obtain the product. Alternatively, multiple amino acid groups may be coupled by the solution method prior to coupling with the resin supported amino acid sequence. The selection of an appropriate coupling reagent is within the skill of the art. A particularly suitable coupling reagent is N,N'-diisopropyl carbodiimide. Another applicable coupling agent is N,N'-dicyclohexylcarbodiimide.

Each protected amino acid or amino acid sequence is introduced into the solid phase reactor in a two to six fold excess and the coupling is carried out in a medium of dimethylformamide: methylene chloride or in either dimethylformamide or methylene chloride alone. In cases where incomplete coupling occurs the coupling procedure is repeated before removal of the α-amino protecting group, prior to introduction of the next amino acid to the solid phase reactor. The success of the coupling reaction at each stage of the synthesis is monitored by the ninhydrin reaction as described by E. Kaiser et al., Analyt. Biochem, 34, 595 (1970).

The necessary α-amino protecting group employed for each amino acid introduced into the polypeptide is preferably tertbutyloxycarbonyl, although any such protecting group may be employed as long as it is not removed under coupling conditions and is readily removed selectively in relation to the other protecting groups present in the molecule under conditions which otherwise do not effect the formed molecule. Additional examples of such α-amino protecting groups from which selection may be made, after consideration of the rest of the polypeptide molecule, are trityl, phthalyl, tosyl, allyloxycarbonyl, cyclopentyloxycarbonyl, tert-amyloxycarbonyl, benzyloxycarbonyl, o and p-nitrobenzyloxycarbonyl and the like.

The fully protected, resin supported nonapeptide presents the amino acid sequence:

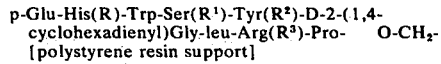

in which the group —O—CH$_2$—[polystyrene resin support] represents the ester moiety of one of the many functional groups present in the polystyrene resin;

R is a protecting group for the imino nitrogen of the histidyl group and $R^3$ is a protecting group for the guanyl function of the arginyl moiety. While the tosyl protecting group is preferred in this capacity, other applicable protecting groups include the acetyl, benzoyl, tert-butyl, trityl, benzyl, benzyl oxycarbonyl, adamantyloxycarbonyl and similar groups. The guanyl function of the arginyl moiety may be protected via the N or N¹ nitrogen atoms by the nitro or tosyl protecting groups and via the N nitrogen atom or either of the N or N¹ nitrogen atom by benzyloxycarbonyl, adamantyloxycarbonyl, trityl, and similar groups; and R¹ and R² are protecting groups for the hydroxyl groups of serine and tyrosine. The hydroxy protecting groups conventionally employed for this purpose are acetyl, tosyl, benzoyl, tert-butyl, trityl, benzyl, benzyloxycarbonyl, 2,6-dichloro-benzyl, and the like, the benzyl and 2,6-dichlorobenzyl groups being preferred for this purpose.

The criterion for selecting protecting groups for R–R³ are (a) the protecting group must be stable to the reagent and under the reaction conditions selected for removing the α-amino protecting group at each step of the synthesis, (b) the protecting group must retain its protecting properties (i.e. not be split off under coupling conditions), and (c) the protecting group must be readily removable upon conclusion of the polypeptide synthesis, under conditions that do not otherwise effect the polypeptide structure.

The fully protected nonapeptide is removed from the resin support by treatment with an amine selected from the group consisting of methylamine, ethylamine, propylamine, 2-propylamine, butylamine, 2-butylamine, pentylamine, 2-pentylamine, 3-pentylamine, phenethylamine or dimethylamine at room temperature followed by removal of any excess of the amine to yield the intermediate of this invention, which is

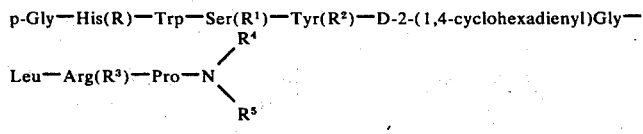

in which

R, R¹, R² and R³ are, independently, acetyl, benzoyl, tert-butyl, trityl, benzyl, 2,6-dichlorobenzyl, benzyloxycarbonyl, adamantyloxycarbonyl, tosyl or nitro;

R⁴ and R⁵ are methyl or R⁴ is hydrogen and

R⁵ is methyl, ethyl, propyl, iso-propyl, butyl, 2-butyl, pentyl, 2-pentyl, 3-pentyl or phenethyl.

The fully protected intermediate described in the preceding paragraph is deprotected with liquid hydrogen fluoride in the presence of anisole to yield the nonapeptide claudogenicinterceptive agents of this invention.

The acid addition salts of the nonapeptides of this invention are produced by known techniques from either inorganic or organic acids known to afford pharmaceutically acceptable non-toxic addition products, such as hydrochloric, hydrobromic, sulfuric, phosphoric, maleic, acetic, citric, benzoic, succinic, malic, ascorbic acid, and the like.

EXAMPLE 1

PREPARATION OF TERT-BUTYLOXYCARBONYLPROLINE RESIN

Following the procedures of Gisin, Helv. Chim. Acta, 56, 1476(1973), tert-butyloxycarbonylproline (18.56 g., 86.3 mmoles) in an ethanol (112 ml.) water (48 ml.) mixture was treated with concentrated aqueous cesium hydrogen carbonate solution until the pH of the solution reached 7. The reaction mixture was stripped and dried by repeated stripping using ethanol, ethanolbenzene, benzene (three times). The foam residue was dried over phosphorous pentoxide, in vacuo at room temperature overnight.

The total product in dimethylformamide (880 ml.) was stirred overnight at 50° C., under nitrogen with Bio-Beads S.X. 1 Resin (chloromethylated capacity 0.89 meq./g.). The filtered resin was washed thoroughly with dimethylformamide (twice), dimethylformamide-10% water (twice), dimethylformamide (twice), methanol (twice), chloroform (thrice) and dried over P₂O₅. Amino acid analysis indicated a substitution on the resin of 0.64 meq./g.

EXAMPLE 2

L-Pyroglutamyl-N$^{im}$-tosyl-L-histidyl-L-tryptophyl-O-benzyl-L-seryl-O-(2,6-dichlorobenzyl)-L-tyrosyl-D-2-(1,4-cyclohexadienyl)glycyl-L-leucyl-N$^g$-tosyl-L-arginyl-L-prolyl acyl resin ester

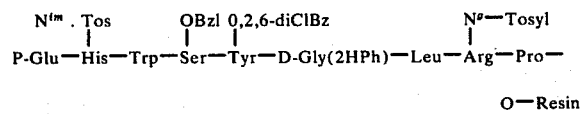

Tert-Butyloxycarbonyl-prolyl acyl resin ester (66.17 g.) in a Merrifield vessel was treated to the following wash cycle (a) methylene chloride-trifluoroacetic acid prewash (5 minutes), (b) methylene chloride-trifluoroacetic acid (2 × 15 minutes), (c) methylene chloride (twice), (d) dimethylformamide, (e) dimethylformamide - 12.5% triethylamine (2 × 10 minutes), (f) dimethylformamide, (g) methylene chloride (twice), (h) methanol (twice), (i) methylene chloride (thrice), allowing a contact time of at least 3 minutes each if not indicated otherwise.

The resin so prepared was gently shaken with tert-butyloxycarbonyl-N$^g$-tosyl arginine (75 meq.) in 1:1 methylene chloride-dimethylformamide during 5 minutes followed by the addition of 1M isopropylcarbodiimide (75 ml., 75 meq.) in two portions 30 minutes apart. Shaking was continued during 18 hours. The peptide resin was washed successively with (j) methanol, (k) methylene chloride, (l) methanol (twice, (m) methylene chloride (twice). Usually to test for completeness of reaction, the peptide-resin was subjected to a ninhydrin test following the procedure of E. Kaiser et al., Analytical Biochemistry 34, 595 (1970). Proline, however, is anomalous giving a weak color reaction in the above test, so the coupling was repeated using 37.5 mmoles tert-butyloxycarbonyl-N-tosyl-arginine and 37.5 mmoles dicyclohexylcarbodiimide.

The following amino acid residues were introduced sequentially onto the washed (steps (j) – (m) ), deprotected and neutralized, (steps (a) – (i) ) peptide resin: First tert- butyloxycarbonyl-L-leucine hydrate(75 meq.), then the synthesis was continued with 6.17 gram aliquot of the peptide-resin, adding tert-butoxycarbonyl-D-2-(1,4-cyclohexadienyl) glycine (9.25 meq.) followed by tert-butyloxycarbonyl-O-(2,6-dichloro-benzyl)-L-tyrosine (9.25 meq.), tert-butyloxycarbonyl-O-benzyl-L-serine (9.25 meq.), tert-butyloxycarbonyl-L-tryptophan (9.25 meq.), tert-butyloxycarbonyl-N-tosyl-L-histidine (9.25 meq.), and L-2-pyrrolidone-5-carboxylic acid (9.25 meq.). After the addition of tryptophan, 0.5% of dithioerythritol was added to the trifluoroacetic acid wash. All couplings were mediated using 10 meq. of 1M isopropylcarbodiimide in methylene chloride as described for the addition of tert-butyloxycarbonyl-$N^g$-tosyl-arginine except for the case of tert-butyloxycarbonyl-L-leucine, the diisopropylcarbodiimide reagent being added first to reduce the possibility of peptide loss via diketo piperazine formation, cf. B. F. Gisin & R. B. Merrifield, J. Amer. Chem. Soc., 94, 3102 (1972). The resin was washed steps (j) –(m) and dried in vacuo to give the title compound.

EXAMPLE 3

L-pyroglutamyl-$N^{im}$-tosyl-L-histidyl-L-tryptophyl-O-benzyl-L-seryl-O-2,6-dichlorobenzyl-L-tyrosyl-D-2-(1,4-cyclohexadienyl)glycyl-L-leucyl-$N^g$-tosyl-L-arginyl-L-prolin-ethylamide Protected peptide-resin (ca. 6.5 g.) from Example 2 and ethylamine (120 ml.) were stirred overnight in a glass pressure bottle. Ethylamine was removed under reduced pressure and the residue washed with methanol, dimethylformamide (four times), methanol and methylene chloride. The combined filtrates were evaporated in vacuo below 35° C. to give the title compound.

By the same or analogous procedures, with the exception that one of dimethylamine, methylamine, propylamine, i-propylamine, butylamine, secondary butylamine, t-butylamine, pentylamine or phenethylamine is substituted for ethylamine, each of the amides corresponding to the amine reactant employed is produced.

EXAMPLE 4

L-pyroglutamyl-L-histidyl-L-tryptophyl-L-seryl-L-tyrosyl-D-2-(1,4-cyclohexadienyl)glycyl-L-leucyl-L-arginyl-L-prolinethylamide The product of Example 3 was treated in vacuo with anhydrous liquid hydrogen fluoride (120 ml.) and anisole (35 ml.) for 50 minutes at 0° C. Hydrogen fluoride was removed under reduced pressure and the residue distributed between diethyl ether and 10% aqueous acetic acid. Lyophyllization of the acid layer afforded the crude title product (2.41 g.).

EXAMPLE 5

Purification and characterization of L-pyroglutamyl-L-histidyl-L-tryptophyl-L-seryl-L-tyrosyl-D-2-(1,4-cyclohexadienyl)glycyl-L-leucyl-L-arginyl-L-prolinethylamide The crude peptide (2.41 g.) in a minimum volume of 0.2N acetic acid was applied to a column of Sephadex G-25 fine previously equilibrated with 0.2 N acetic acid and then eluted with the same solvent. Fractions of 9 ml. each were collected. Peptide material was located by Ehrlich spot test and UV analysis. One major fraction was obtained, 35–56 (1.724 g.). This material was rechromatographed on a partition column of Sephadex G-25 fine (2.5 × 100 cm.) prepared by equilibration with lower phase and then upper phase of the BAW system (n-butanol:acetic acid:water, 4:1:5). Elution with upper phase afforded fractions A 26–41 (608 mg.), B 42–56 (528 mg.). Fraction A was rechromatographed twice using the same system which afforded 188 mg. of the desired peptide.

The Rf value of the peptide (30 ug load) in the thin layer system (silica plates-Brinkman) n-butanol:acetic acid:water (4:1:5, upper phase). Rf 0.11.

The optical rotation measured on a Carl Zeiss LEP A-2 chotpelectric precision polarimeter, $[\alpha]_D^{26}$ = −57.66° (c=1.036, 1% acetic acid).

Hydrolysis of the peptide in methanesulfonic acid (0.2 ml/1 mg. peptide) for 20 hours at 110° C in a closed evacuated system: Ser (0.89), Glu (0.95), Pro (0.99), Leu (1.00), Tyr (0.93), His (0.94), Trp (0.74), ethylamine (0.99), Arg (1.13). 2-(1,4-cyclohexadienyl)glycine is unstable to acidic hydrolysis conditions and results in a pattern of 4-components. The presence of these same 4 components could be established in the above hydrolysate.

What is claimed is:

1. A compound of the formula:

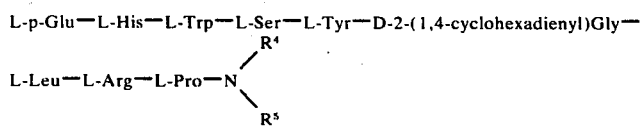

in which $R^4$ and $R^5$ are methyl or $R^4$ is hydrogen and $R^5$ is alkyl of 1 to 5 carbon atoms or phenethyl, or a non-toxic acid addition salt thereof.

2. A compound of claim 1 of the formula: L-p-Glu-L-His-L-Trp-L-Ser-L-Tyr-D-2-(1,4-cyclohexadienyl)Gly-L-Leu-L-Arg-L-Pro-NHC$_2$H$_5$, or a non-toxic acid addition salt thereof.

3. The compound of claim 1 which is L-p-Glu-L-His-L-Trp-L-Ser-L-Tyr-D-2-(1,4-cyclohexadienyl)Gly-L-Leu-L-Arg-L-Pro-NHC$_2$H$_5$.

4. A compound of the formula: L-p-Glu-L-His(R)-L-Trp-L-Ser($R^1$)-L-Tyr($R^2$)-D-2-(1,4-cyclohexadienyl)Gly-L-Leu-L-Arg($R^3$)-L-Pro-X in which R, $R^1$, $R^2$ and $R^3$ are, independently, acetyl, benzoyl, tert-butyl, trityl, benzyl, 2,6-dichlorobenzyl, benzyloxycarbonyl, adamantyloxycarbonyl, tosyl or nitro; and X is —O—CH$_2$-[polystyrene resin support] or

in which $R^4$ and $R^5$ are methyl or $R^4$ is hydrogen and $R^5$ is alkyl of 1 to 5 carbon atoms or phenethyl; or a pharmaceutically acceptable acid addition salt thereof.

5. A compound of claim 4 in which R and $R^3$ are tosyl, $R^1$ is benzyl $R^2$ is 2,6-dichlorobenzyl and X is —O—CH$_2$-[polystyrene resin support] or

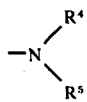

in which $R^4$ and $R^5$ are methyl or $R^4$ is hydrogen and $R^5$ is alkyl of 1 to 5 carbon atoms or phenethyl.

6. A method for terminating pregnancy in a female mammal which comprises administering a nonapeptide of the formula,

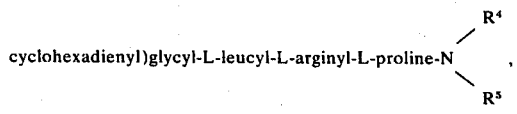

in which $R^4$ and $R^5$ are methyl or $R^4$ is hydrogen and $R^5$ is alkyl of 1 to 5 carbon atoms or phenethyl, or a nontoxic acid addition salt thereof, to said mammal, post coitally, in a daily regimen containing at least about 600 microgram per kilogram host body weight for a time sufficient to terminate pregnancy.

7. The method of claim 6 in which said nonapeptide is administered, orally or parenterally, to said mammal following a daily regimen beginning on day one after coitus and extending through about the first eight days post implantation.

8. The method of claim 6 in which said nonapeptide is administered, orally or parenterally, following a daily regimen beginning on day one after coitus and extending through about day seven post coitus.

9. The method of claim 6 in which said nonapeptide is administered, orally or parenterally, following a daily regimen beginning after implantation and extending through the luteal phase of the menstrual cycle.

* * * * *